United States Patent [19]

Samson

[11] Patent Number: 4,516,972
[45] Date of Patent: May 14, 1985

[54] GUIDING CATHETER AND METHOD OF MANUFACTURE

[75] Inventor: Wilfred J. Samson, Saratoga, Calif.

[73] Assignee: Advanced Cardiovascular Systems, Inc., Mountain View, Calif.

[21] Appl. No.: 522,833

[22] Filed: Aug. 12, 1983

Related U.S. Application Data

[63] Continuation-in-part of Ser. No. 343,588, Jan. 28, 1982, abandoned.

[51] Int. Cl.³ .............................................. A61M 5/00
[52] U.S. Cl. ..................................... 604/282; 138/130
[58] Field of Search ........................ 604/282, 280, 95; 138/130, 132

[56] References Cited

U.S. PATENT DOCUMENTS

| | | | |
|---|---|---|---|
| 2,407,929 | 9/1946 | Jeckel | 604/282 X |
| 2,437,542 | 3/1948 | Krippendorf | 604/282 X |
| 3,416,531 | 12/1968 | Edwards | 604/282 X |
| 3,924,632 | 12/1975 | Cook | 604/282 |

Primary Examiner—Stephen C. Pellegrino
Attorney, Agent, or Firm—Flehr, Hohbach, Test, Albritton & Herbert

[57] ABSTRACT

Catheter for insertion into the cardiovascular system, and method of manufacturing the same. A helically wound ribbon of flexible material is imbedded in the wall of the catheter to provide a torsional rigidity which facilitates steering and turning of the catheter during emplacement. The stiffness of the catheter is controlled by varying the pitch of the helically wound ribbon.

6 Claims, 3 Drawing Figures

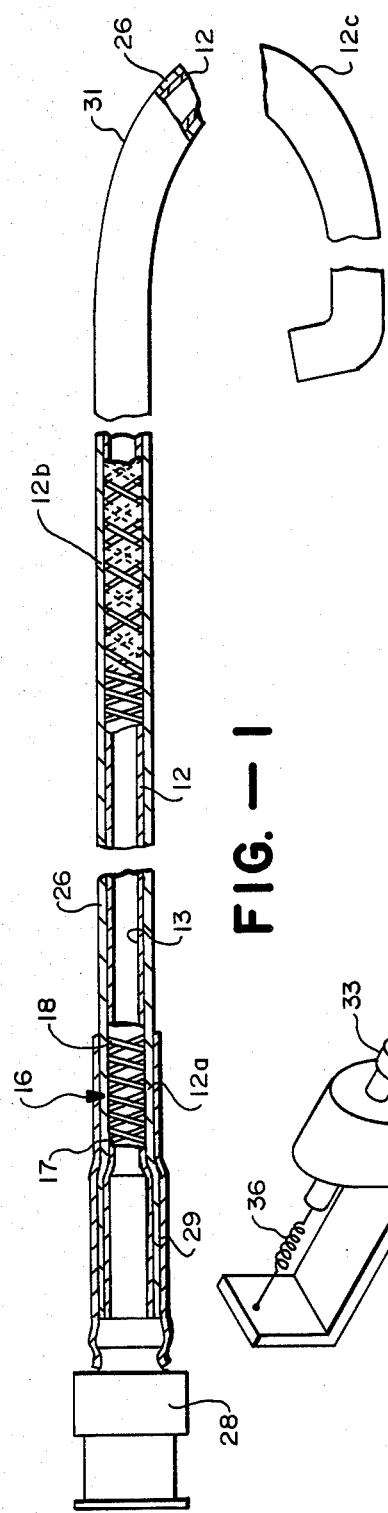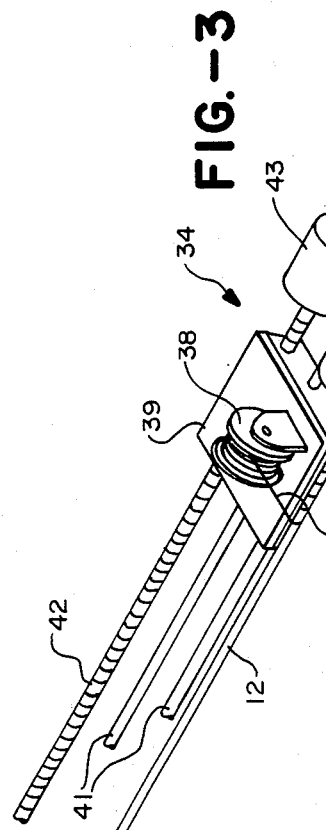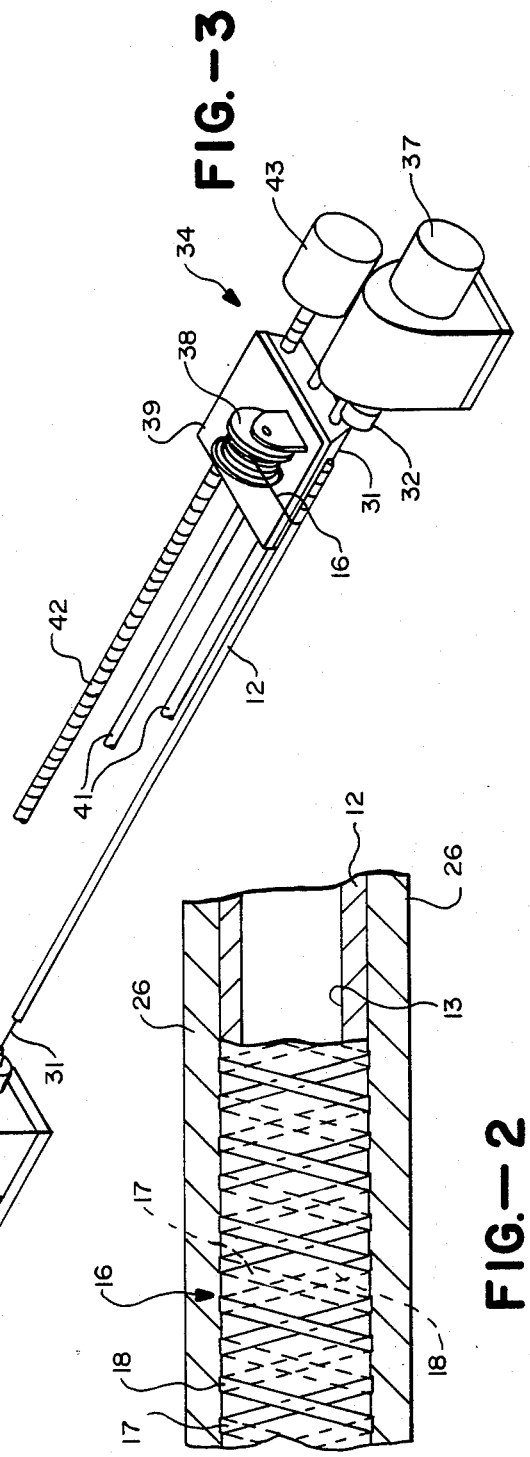

GUIDING CATHETER AND METHOD OF MANUFACTURE

This is a continuation-in-part of application Ser. No. 343,588, filed Jan. 28, 1982 now abandoned.

This invention pertains generally to catheters for insertion into the cardiovascular system, and more particularly to a catheter which can be steered or turned as it is inserted and to a method of manufacturing the same.

Guiding catheters and other catheters (e.g., balloon catheters and angiographic catheters) which are inserted into the cardiovascular system must, at times, be turned and steered in order to achieve the desired placement. With many catheters heretofore provided, this process is difficult because the catheters tend to twist and untwist in an unpredictable manner as they are turned in an effort to steer them.

In an attempt to overcome this problem, some catheters have been provided with a wire braid (e.g., stainless steel) imbedded in the wall of the catheter. While the wire braid does provide some torsional stiffening, and therefore better control, the wire tends to be brittle and difficult to handle in the manufacturing process if made fine enough not to increase the thickness of the wall by an appreciable amount. While the use of a heavier wire might overcome the problem of breakage, it would require a thicker wall and would, therefore, increase the outer diameter of the catheter and/or decrease the size of the central passageway or lumen. Either of these alternatives would be contrary to the fundamental objective of providing the largest possible lumen and the smallest possible outer diameter so that the catheter will fit in a relatively small opening in the body. In addition, the manufacture of a catheter having a wire braid imbedded therein is relatively time consuming and expensive.

It is in general an object of the invention to provide a new and improved cardiovascular catheter and method of manufacturing the same.

Another object of the invention is to provide a catheter of the above character having a high burst pressure during high pressure angiographic injections (typically as high as 1600 psi) while retaining a relatively thin wall.

Another object of the invention is to provide a catheter and method of the above character in which the torsional rigidity of the catheter can be varied along the length of the catheter.

Another object of the invention is to provide a catheter of the above character which is manufactured by the use of preimpregnated fibres.

These and other objects are achieved in accordance with the invention by providing a catheter and a method of manufacturing the same wherein a length of flexible filament is wound or a plurality of filaments are wound simultaneously in helical fashion about the lumen or passageway of the catheter. In one embodiment, the flexible filament is wrapped about a tubular inner liner which defines the lumen, an outer jacket is formed over the filament, and the inner liner, the filament and the outer jacket are bonded together to form a unitary structure with torsional rigidity. The pitch of the helically wound filament can be varied along the length of the liner to vary the stiffness of the catheter.

FIG. 1 is an enlarged elevational view, with portions in cross section, of one embodiment of a cardiovascular catheter incorporating the invention.

FIG. 2 is a further enlargement of the cross sectional portion shown in FIG. 1.

FIG. 3 is an isometric view, somewhat schematic, of apparatus employed in one embodiment of a method of manufacturing the catheter of FIG. 1.

The guiding catheter 11 of the present invention is adapted to be inserted into a body passage of a patient. The distal end is adapted to be inserted into the body passage whereas the proximal end is adapted to remain outside the body passage. As illustrated in FIG. 1, the catheter 11 comprises an elongate flexible tubular inner liner or member 12 which defines an axially extending passageway or lumen 13. The liner 12 is provided with an outer cylindrical surface 14. The liner 12 is fabricated of a suitable flexible, relatively unctuous (slippery) material such as polytetrofluoroethylene (Teflon) or nylon, with a relatively thin wall thickness, e.g., 0.003–0.005 inch and an inner diameter of 0.075–0.080 inch. However, inner liners having an inside diameter ranging from 0.052 to 0.130 inches can be used.

An elongate ribbon 16 of flexible material is wrapped or a plurality of ribbons, i.e., five or more are wrapped in parallel in helical fashion onto the outer surface 14 of the liner 12 to provide torsional rigidity to the catheter facilitating steering and turning of the catheter in the body passage. The ribbon 16 is wrapped or a plurality of ribbons are wrapped in at least first and second successive layers 17 and 18. The first layer 17 is formed by winding the ribbon 16 or ribbons helically in a first single layer in one direction onto the exterior surface 14 of the tubular member 12. The layer 18 is formed by winding the ribbon 16 or ribbons in a second single layer helically in an opposite direction onto the exterior surface 14 of the tubular member 12 and over the first single layer 17 as shown in detail in FIG. 2.

The ribbon 16 should preferably be formed of a high tensile strength flexible material. One material found to be particularly satisfactory is "Kevlar 49" Aramid yarns supplied by DuPont in various fineness ranging from 195 to 2130 denier. "Kevlar 49" is particularly useful with plastics. If lower denier yarns become available, their use would be desirable. It has a high tensile strength of 400,000 lb/in$^2$ and a high modulus of 18 million lb/in$^2$. The yarns are composed of multiple round cross section continuous filaments of almost 1.5 denier per filament. The combination of high tensile strength and modulus with the 0.052 lb/in$^3$ (1.44 g/cm$^3$) density provides a higher specific tensile strength than most if not all commercially available materials and a specific modulus between that of fiberglass and boron and graphite fibers. "Kevlar 49" fibers have excellent toughness. In one guiding catheter 380 denier "Kevlar 49" was used in which the ribbon had cross sectional dimensions of 2.5×50 mils. In addition 195 denier "Kevlar 49" has also been used having smaller cross sectional dimensions of 2×40 mils.

In certain applications other filaments having high tensile strength and flexibility such as carbon and boron can be used. In order to obtain variations in torsional rigidity and stiffness of the catheter, the the pitch or density of the helical winding of the ribbon can be changed. Multiple ribbons as hereinbefore explained can be used. Thus, as shown in FIG. 1, a higher density or pitch can be used at the proximal end portion 12a of the catheter to an intermediate portion 12b of the catheter and a lower density or pitch from the intermediate portion to near the distal end portion 12c. To provide for a more flexible tip to the catheter 11, the ribbon 16 is not wound onto the distal end portion 12c of the catheter 11.

The ribbons forming the windings or layers 17 and 18 are bonded to the outer surface of the flexible tubular member 12 in a suitable manner such as by use of an epoxy.

An outer jacket 26 of flexible material is formed over the first and second layers 17 and 18 and encases or encapsulates the layers 17 and 18. This jacket 26 is fabricated of a thermoplastic material such as polyethylene which can be sterilized so as not to contaminate the body into which it is inserted. In one presently preferred embodiment, the outer jacket is fabricated of a heat shrinkable tubing which is formed tightly over the layers 17 and 18 encircling the flexible tubular member 12.

Inner liner 12, filament 16 and outer jacket 26 are bonded together by suitable means such as by a conventional epoxy to form a unitary structure. The unitary nature of the structure has been found to improve the torsional rigidity of the catheter and thereby facilitates turning and steering of the catheter 11 during emplacement in the body.

A suitable connector or fitting 28, such as a female Luer fitting, is inserted into the inlet or proximal end of the catheter and is secured therein by a heat shrinkable sleeve 29 extending over the fitting 28 and the proximal end portion of the liner 12 and the outer jacket 26. As shown, the distal end portion 31 of the catheter can be formed with the desired bend used in conventional guiding catheters.

Referring now to FIG. 3, a preferred method of manufacturing the catheter is illustrated. Inner liner or tubular member 12 is mounted on a wire-like mandrel 31 which extends axially through the opening in the tubing which forms the liner. To facilitate later removal, a lubricant such as silicon is applied to the mandrel before it is inserted into the tubing. The tubing is then temporarily affixed to the mandrel by suitable means, and in presently preferred embodiment the liner is fabricated of a heat shrinkable tubing which is heated and shrunk about the mandrel.

Mandrel 31 is mounted between the chucks 32, 33 or a winding machine 34 and drawn taut by suitable means such as a spring 36. A drive motor 37 is connected to chuck 32 to rotate the same about its axis, and chuck 33 is provided with a bearing which permits it to turn freely about its axis.

A spool 38 holding a ribbon 16 or multiple spools holding a plurality of ribbons to be wrapped about the member 12 is or are rotatably mounted on a carriage 39. This carriage is mounted on ways 41 for movement in a longitudinal direction between the chucks and is driven by a lead screw 42 and a reversible, variable speed drive motor 43.

Before the ribbon 16 is wound on the liner, the outer surface of the member 12 is cleaned (e.g., by etching), and a bonding agent such as epoxy is applied to the cleaned surface. The ribbon 16 is affixed to the member 12 near one end thereof, and drive motor 37 is energized to turn the mandrel about its axis and thereby wind the ribbon 16 onto the member 12. Multiple ribbons as hereinbefore described can be applied in parallel in the same manner. Drive motor 43 is also energized to move carriage 39 toward the other end of the member 12. As the carriage travels, the ribbon 16 is wound onto the member 12 in helical fashion, with a pitch determined by the relative speeds of the two drive motors. With winding motor 37 turning at a relatively constant speed, the pitch of the winding is controlled by varying the speed of carriage motor 43.

For the catheter of FIG. 1, the first layer 17 of single or multiple ribbons is wound onto the tubular member 12 as the carriage travels from one end of the member 12 to the other in one direction. When the first layer 17 is completed, the direction of carriage travel is reversed, and the second layer 18 of single or multiple ribbons is wound in an opposite helical direction over the first layer 17 as the carriage returns to the starting position. In this embodiment, the speed of the carriage motor 43 is increased for a greater pitch or density of the windings and decreased for a less dense pitch or density of the windings.

When the winding operation is completed, an additional conventional bonding agent is applied to the second or outer layer 18, and outer jacket 26 is installed. In one presently preferred embodiment, the outer jacket comprises a length of heat shrinkable tubing which is placed over the first and second layers or windings and 18 and then heated to shrink it onto the layers 17 and 18 and the tubular member 12. Alternatively, the bonding agent can be applied to the ribbon 16 before it is wrapped about the liner or tubular member 12, in which case it is not necessary to make separate applications of the bonding agent to the liner and to the first layer 17 of ribbon 16. With the use of preimpregnated ribbons or filaments, the use of an epoxy is limited to the distal tip region of the catheter where few or no filaments or ribbons are used and therefore little or no epoxy is present.

After the bonding agent has cured the mandrel is removed from the central passageway, the catheter is cut to length, connector 28 is installed, and the desired bend formed in the distal end of the catheter.

Rather than using a separate inner liner or tubular member 12, the filament can be impregnated with epoxy or another suitable material and wound directly onto the winding mandrel in first and second layers. The outer jacket can then be formed over the first and second layers of ribbons as discussed above, following which the mandrel can be removed to provide the central passageway or lumen.

The invention has a number of important features and advantages. The helically wound ribbons and the unitary structure of the catheter give the catheter a torsional rigidity which make it relatively easy to turn and steer as it is inserted into the body passage. The catheter has a relatively thin wall and the stiffness and torsional rigidity of the catheter can be varied by varying the pitch of the helical wound ribbons. In addition, the catheter can be manufactured quickly and economically.

It is apparent from the foregoing that a new and improved catheter and method of manufacturing the same have been provided. While only certain presently preferred embodiments have been described in detail, as will be apparent to those familiar with the art, certain changes and modifications can be made without departing from the scope of the invention as defined by the following claims.

I claim:

1. In a guiding catheter for insertion into a body passage of a patient, an elongate flexible tubular plastic member having a lumen extending therethrough, the member having a distal end adapted to be inserted into the body passage and a proximal end adapted to remain outside the body passage, a flat flexible ribbon wound helically in a first single layer in one direction onto the exterior of the tubular plastic member and a second single layer overlying the first layer and wound helically in an opposite direction onto the exterior of the tubular plastic member, each of the first and second layers having different pitches in different regions along the length of the tubular plastic member, means bonding the helically wound ribbon to the exterior surface of the plastic member, said first and second layers of ribbon providing torsional rigidity to the catheter facilitating steering and turning of the catheter in the body passage, and an outer flexible tube formed of a heat shrinkable material shrunk onto said elongate flexible tubular member with the ribbons bonded thereto to form a unitary assembly.

2. A catheter as in claim 1 in which the ribbon is formed of aromatic polyamide filaments.

3. A catheter as in claim 2 in which the aromatic polyamide filaments are Kevlar 49 supplied by DuPont.

4. A catheter as in claim 3 wherein the ribbon is Kevlar 49 yarn ranging from approximately 195 to 380 denier.

5. In a method for manufacturing a guiding catheter for insertion into a body passage of a patient, providing an elongate flexible tubular plastic member having a lumen extending therethrough, the member having a distal end adapted to be inserted into the body passage and a proximal end adapted to remain outside the body passage, providing a flat flexible ribbon, winding the flat flexible ribbon onto the outer surface of the tubular plastic member by winding the same helically in a first single layer in one direction onto the same and winding the same helically in an opposite direction in a second single layer overlying the first single layer, forming the helices of the flat flexible ribbon of different pitches in different regions along the length of the flexible tubular member, bonding the flat flexible ribbons to the flexible tubular plastic member, providing an outer tubing formed of a heat shrinkable material, mounting the tubing of heat shrinkable material over the tubular plastic member with the flat flexible ribbons wound thereon and applying heat to the outer tubing to cause it to shrink onto the tubular plastic member having the ribbon wrapped thereon to form the same into a unitary assembly.

6. A method as in claim 5 together with the step of wrapping the ribbon about the tubular plastic member at different pitches in different regions along the length of the plastic tubular member, said flat flexible ribbons being wound so that they are tensioned so that the ribbons provide torsional rigidity to the catheter facilitating steering and turning of the catheter in the body passage.

* * * * *